United States Patent
Lena et al.

(10) Patent No.: US 11,939,342 B2
(45) Date of Patent: Mar. 26, 2024

(54) PROCESS FOR THE PREPARATION OF MIDOSTAURIN WITH HIGH PURITY

(71) Applicant: PROCOS S.P.A., Cameri (IT)

(72) Inventors: Alberto Lena, Cameri (IT); Antonio Toppino, Cameri (IT); Katia Miele, Settala (IT); Jacopo Roletto, Cameri (IT); Paolo Paissoni, Cameri (IT)

(73) Assignee: PROCOS S.P.A., Cameri (IT)

( * ) Notice: Subject to any disclaimer, the term of this patent is extended or adjusted under 35 U.S.C. 154(b) by 504 days.

(21) Appl. No.: 17/426,356

(22) PCT Filed: Mar. 25, 2020

(86) PCT No.: PCT/EP2020/058273
§ 371 (c)(1),
(2) Date: Jul. 28, 2021

(87) PCT Pub. No.: WO2020/200945
PCT Pub. Date: Oct. 8, 2020

(65) Prior Publication Data
US 2022/0098216 A1    Mar. 31, 2022

(30) Foreign Application Priority Data
Mar. 29, 2019 (IT) .......................... 102019000004729

(51) Int. Cl.
*C07D 498/22* (2006.01)

(52) U.S. Cl.
CPC .................................. *C07D 498/22* (2013.01)

(58) Field of Classification Search
None
See application file for complete search history.

(56) References Cited

U.S. PATENT DOCUMENTS 5,093,330 A    3/1992    Caravatti et al.

FOREIGN PATENT DOCUMENTS

| EP | 0575955 A1 | 12/1993 |
| JP | 5247055 B2 | 7/2013 |
| WO | 2006048296 A1 | 5/2006 |
| WO | 2011064355 A1 | 6/2011 |
| WO | 2018165071 A1 | 9/2018 |

OTHER PUBLICATIONS

International Search Report and Written Opinion for Corresponding International Application No. PCT/EP2020/058273 (dated Jun. 12, 2020) (12 pages).

*Primary Examiner* — Samantha L Shterengarts
(74) *Attorney, Agent, or Firm* — Lucas & Mercanti, LLP

(57) ABSTRACT

A process for the preparation of midostaurin with high purity, particularly a process for the preparation of midostaurin with a content of oxidation impurities lower than 0.1% comprising the treatment of crude midostaurin or staurosporine with strong organic or inorganic acids in a water-immiscible solvent and, optionally, also with reducing silanes is described.

17 Claims, No Drawings

PROCESS FOR THE PREPARATION OF MIDOSTAURIN WITH HIGH PURITY

CROSS-REFERENCE TO RELATED APPLICATIONS

This application is a 371 of PCT/EP2020/058273, filed Mar. 25, 2020, which claims the benefit of Italian Patent Application No. 102019000004729, filed Mar. 29, 2019.

The present invention relates to a process for the preparation of midostaurin with high purity, particularly a process for the preparation of midostaurin with a content of oxidation impurities lower than 0.1%.

BACKGROUND OF THE INVENTION

Midostaurin is an anti-tumoral drug authorized by FDA and EMA in 2017 for the treatment of adults with Acute Myeloid Leukaemia (AML) and for the treatment of adults with aggressive systemic mastocytosis, systemic mastocytosis associated with a haematological neoplasm and mast cell leukaemia.

The active ingredient midostaurin (INN), also known as N-benzoyl staurosporine or PKC-412, has the following formula I

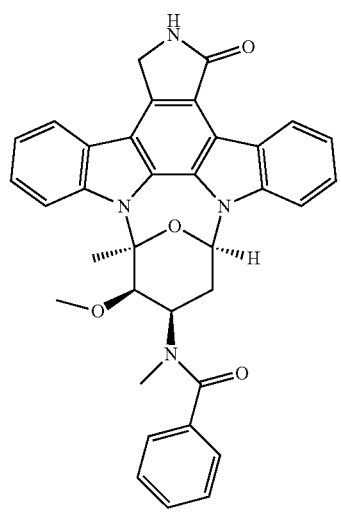

(I)

and is on the market under the name Rydapt® as pharmaceutical preparation in capsule form for oral administration.

Even if it has been recently authorized as anti-tumoral drug, midostaurin is a compound known since some decades and it is prepared by semi-synthesis from staurosporine, an alkaloid produced by fermentation from the bacterium *Streptomyces staurosporeus*, through a benzoylation reaction (see, for example, U.S. Pat. No. 5,093,330 and JP5247055) as depicted in scheme 1.

Scheme 1

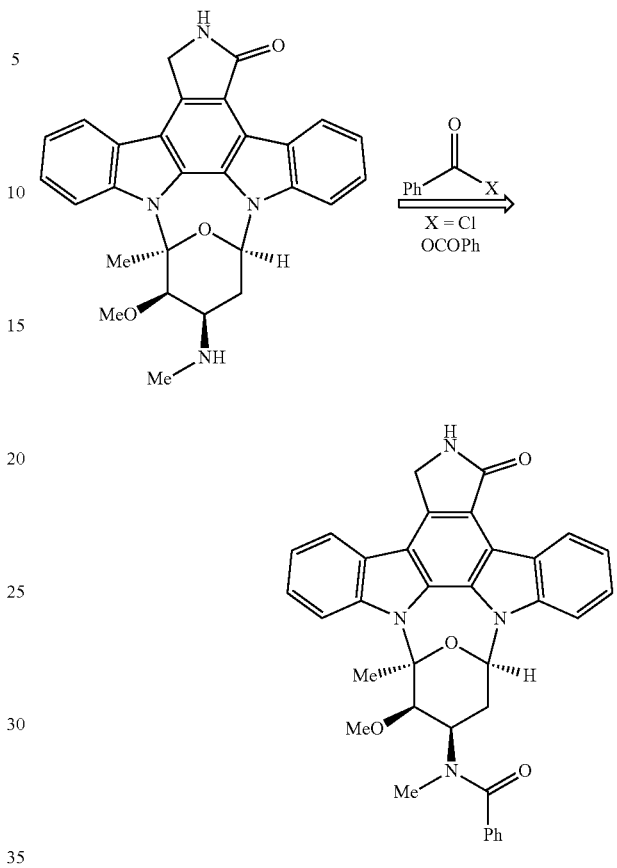

Whilst there is a broad literature about midostaurin and its use as anti-tumoral drug, the literature related to synthetic strategies, solid forms and impurities as well as the information related to the impurities of staurosporine are rather limited.

In WO2006048296, disclosing midostaurin crystalline form II, it is reported that said crystalline form is synthetized starting from staurosporine previously purified by treatment with methanesulfonic acid in an alcohol solvent. There is no mention of oxidation impurities in WO2006048296 and therefore this problem is not addressed or solved. Moreover, the use of methanesulfonic acid in the presence of an alcohol results in additional impurity problems due to the formation of toxic methanesulfonic esters.

WO2011064355 and WO2018165071 disclose several midostaurin crystalline forms (form III, IV, V, VI, VII, VIII, IX, X, XI, XII, XIII, XIV, XV, XVI) obtained by using compressed $CO_2$ or different crystallization solvents.

Furthermore, there are several studies in the literature related to the identification and to the pharmacokinetic study of the primary midostaurin metabolites. The papers Bioorganic & Medicinal Chemistry Letters, 1994, 4(3), 399-404 and Clinical Pharmacokinetics, 2008, 47(12), 807-816 disclose two diastereomers of 3-hydroxymidostaurin (III) and (IV), an oxidized form of midostaurin on the isoindoline methylene, among said metabolites. In Biochemistry, 2018, 57(38), 5576-5590, the absolute configuration of said two metabolites (III) and (IV) has been assigned for the first time.

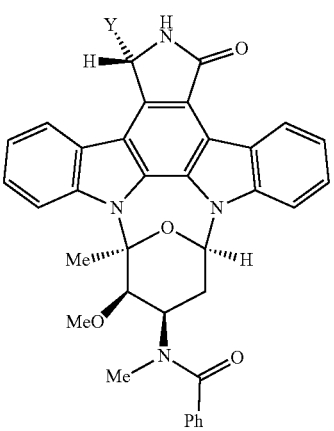

|  | X | Y |
|---|---|---|
| (III) 3-R-hydroxymidostaurin | OH | H |
| (IV) 3-S-hydroxymidostaurin | H | OH |

As for the analogous oxidized staurosporine derivatives, EP 0 575 955 discloses a process for the synthesis of 3-hydroxystaurosporine, as a mixture of two diastereomers 3-R and 3-S of formula (V) and (VI).

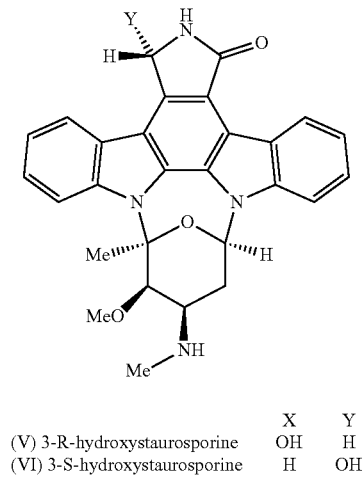

|  | X | Y |
|---|---|---|
| (V) 3-R-hydroxystaurosporine | OH | H |
| (VI) 3-S-hydroxystaurosporine | H | OH |

The Applicant observed that the staurosporine derivatives (V) and (VI) already form during the fermentation step and that, in the subsequent process for obtaining midostaurin, they are transformed into the corresponding benzoylated derivatives (III) and (IV) with a concurrent increase.

There are no references in the prior art related to the formation and to the structure of process impurities in the manufacturing of midostaurin and staurosporine. Even if the oxidized 3-hydroxymidostaurin (III) and (IV) and 3-hydroxystaurosporine (V) and (VI) derivatives are known compounds, the prior art does not acknowledge said metabolites as process impurities or much less discloses any methods for limiting them.

The Applicant also observed that the quenching methods of the benzoylation reaction disclosed in the literature (for example by using water or a bicarbonate solution) result in a significant increase (even some decimal points) of the midostaurin oxidation impurities.

Moreover, no known midostaurin crystallization processes allow to effectively remove or at least decrease such impurities below the 0.1% limit, unless several crystallizations are carried out with resulting high losses in yields and in manufacturing process efficiency.

Furthermore, the long term stability tests of midostaurin at air and under stressed conditions showed a significant increase of the oxidation impurities. This requires the obtainment of purified midostaurin with the lowest as possible content of said impurities, in order to minimize the risk that they exceed the 0.1% limit in time. Then, there is a purity and stability problem for midostaurin due to the formation and presence of oxidation impurities. This problem results in the need to find an efficient and industrially applicable method to decrease the oxidation impurities as well as a quenching procedure for the benzoylation reaction which limits their formation during the transformation of staurosporine into midostaurin.

DESCRIPTION OF THE INVENTION

The Applicant has now found that the content of oxidation impurities (III) and (IV) in midostaurin or the content of oxidation impurities (V) and (VI) in staurosporine can be decreased thereby obtaining purified midostaurin with a content of 3-hydroxymidostaurin impurities (III) and (IV) lower than 0.1%.

Such a decrease in the content of the oxidation impurities is achieved by treating said impurities with strong organic or inorganic acids in a water-immiscible solvent and optionally also with reducing silanes.

The Applicant has also found a quenching method of the benzoylation reaction which uses an aqueous solution having a slightly acid pH allowing to limit the formation and/or the increase of the oxidation impurities (III) and (IV) during the transformation process of staurosporine into midostaurin.

Therefore, a first object of the present invention is a process for the preparation of midostaurin with high purity, that is with a content of 3-hydroxymidostaurin impurities (III) and (IV) lower than 0.1%, comprising the treatment of crude midostaurin with a reducing silane in the presence of a strong organic or inorganic acid in a water-immiscible solvent.

A further object of the present invention is a process for the preparation of midostaurin with high purity, that is with a content of 3-hydroxymidostaurin impurities (III) and (IV) lower than 0.1%, comprising the treatment of crude staurosporine with a strong organic or inorganic acid in a water-immiscible solvent optionally with the concomitant addition of a reducing silane.

The resulting purified staurosporine can be transformed into midostaurin by benzoylation.

In a preferred embodiment of the present invention, the benzoylation reaction is quenched by treatment with an aqueous solution having a slightly acid pH. Therefore, a further object of the present invention is a process for the preparation of midostaurin with high purity, that is with a content of 3-hydroxymidostaurin impurities (III) and (IV) lower than 0.1%, comprising the benzoylation reaction of staurosporine to midostaurin characterized in that the benzoylation reaction is quenched with an aqueous solution having a slightly acid pH.

In the present context, unless otherwise indicated, the term crude staurosporine means a solid composition containing staurosporine>98% and 3-hydroxystaurosporine>0.1%; the term purified staurosporine means a solid composition containing staurosporine>99% and 3-hydroxystaurosporine≤0.1%; the term crude midostaurin means a solid composition containing midostaurin>98% and 3-hydroxymidostaurin>0.1%; the term purified midostaurin means a solid composition containing midostaurin>99% and 3-hydroxymidostaurin≤0.1%.

DETAILED DESCRIPTION OF THE INVENTION

In one embodiment of the present invention, purified midostaurin having a content of 3-hydroxymidostaurin impurities (III) and (IV) lower than 0.1% is obtained starting from crude midostaurin, which is in turn directly obtainable from crude staurosporine by any one of the processes disclosed in the literature.

Purified midostaurin can be obtained starting from crude midostaurin by carrying out the following steps:
 a) forming a mixture of crude midostaurin and a first water-immiscible solvent,
 b) adding a reducing silane and a strong organic or inorganic acid,
 c) subsequently adding a base and a second solvent,
 d) separating the organic phase and isolating purified midostaurin.

The mixture of step a) can be a solution or a suspension.

The first solvent is an aprotic polar water-immiscible solvent. Examples of aprotic polar water-immiscible solvents are dichloromethane (DCM), dichloroethane (DCE), methyl tetrahydrofuran (Me-THF), methylethylketone (MEK), preferably DCM.

Examples of reducing silanes are triethylsilane, triphenylsilane, diphenylsilane, preferably triethylsilane.

Examples of strong organic or inorganic acids are trifluoroacetic acid (TFA), para toluenesulfonic acid (PTSA), trimethylsilyltriflate, phosphoric acid, preferably trifluoroacetic acid (TFA).

The base can be an organic or inorganic base such as for example sodium hydroxide (NaOH), sodium bicarbonate (NaHCO$_3$), triethylamine (TEA), diisopropylamine (DIPEA), preferably sodium bicarbonate (NaHCO$_3$).

The second solvent can be water or an alcohol/water mixture, preferably water.

An aqueous sodium bicarbonate solution is more preferably used.

After separation of the organic phase, the isolation of the resulting purified midostaurin can be carried out by conventional techniques, preferably by changing the solvent to 2-methyl-tetrahydrofuran (2-MeTHF), dissolving by heating, crystallizing by cooling and subsequently filtering.

The Applicant observed that the solid midostaurin obtained by crystallization from 2-MeTHF, independently from the cooling curve which is used, contains 5 to 10% by weight of residual solvent. Also following drying under vacuum at 80° C., after 3 days the content of 2-MeTHF remains higher than 2%.

Within the scope of the present invention, the Applicant found a method for decreasing the content of residual organic solvents in purified midostaurin below 50 ppm.

A preferred object of the present invention is a process for obtaining purified midostaurin wherein the isolation of purified midostaurin is carried out by crystallization from 2-MeTHF and further comprises:
 e) dissolving the crystallized midostaurin in a water-miscible polar solvent,
 f) adding water
 g) isolating purified midostaurin as an amorphous solid with a content o residual organic solvents<50 ppm by filtering and drying.

The water-miscible polar solvent is preferably selected among ethanol, DMSO and DMF.

In another embodiment of the present invention, purified midostaurin can be also obtained starting from purified staurosporine.

Purified staurosporine can be obtained starting from crude staurosporine by carrying out the following steps:
 a) forming a mixture of crude staurosporine and a first water-immiscible solvent,
 b) adding a reducing silane and a strong organic or inorganic acid,
 c) subsequently adding a base and a second solvent,
 d) separating the organic phase and isolating purified staurosporine.

The mixture of step a) can be a solution or a suspension.

The first solvent is an aprotic polar water-immiscible solvent. Examples of aprotic polar water-immiscible solvents are dichloromethane (DCM), dichloroethane (DCE), methyl tetrahydrofuran (Me-THF), methylethylketone (MEK), preferably DCM. Examples of reducing silanes are triethylsilane, triphenylsilane, diphenylsilane, preferably triethylsilane.

Examples of strong organic or inorganic acids are trifluoroacetic acid (TFA), para toluenesulfonic acid (PTSA), trimethylsilyltriflate, phosphoric acid, preferably trifluoroacetic acid (TFA).

The base can be an organic or inorganic base such as for example sodium hydroxide (NaOH), sodium bicarbonate (NaHCO$_3$), triethylamine (TEA), diisopropylamine (DIPEA), preferably sodium bicarbonate (NaHCO$_3$).

An aqueous sodium bicarbonate solution is preferably used.

The second solvent can be water or an alcohol/water mixture, preferably methanol/water.

The isolation of the purified staurosporine can be carried out by concentrating the organic phase and filtering the resulting solid suspension or by changing the solvent to 2-MeTHF, dissolving by heating, crystallizing by cooling and subsequently filtering. Alternatively, the preparation of purified staurosporine can be also carried out by using a strong organic or inorganic acid only, in step b), that is without adding a reducing silane.

Contrary to the procedure using a reducing silane wherein the in situ reduction of 3-hydroxystaurosporine to staurosporine occurs, in the procedure without silanes, the derivatization of 3-hydroxystaurosporine and the concurrent consumption of 1 staurosporine molecule each molecule of derivatized 3-hydroxystaurosporine occur. The derivatives formed with crude staurosporine during the reaction with the strong acid, preferably TFA, resulted to be easily removable by crystallization in 2-MeTHF. In a preferred embodiment of the present invention, purified midostaurin is obtained by benzoylation reaction starting from purified staurosporine, while keeping the content of oxidation impurities unchanged (<0.1%), by using an aqueous solution with slightly acid pH during the quenching step of the benzoylation reaction.

In details, the process for the preparation of purified midostaurin comprises the following step:
 i) forming a mixture of purified staurosporine and DMF,
 ii) adding DIPEA and benzoyl chloride
 iii) subsequently adding an aqueous solution having slightly acid pH,
 iv) filtering the solid and isolating the purified midostaurin.

The mixture of step i) can be a solution or a suspension.

The aqueous solution having slightly acid pH is preferably an aqueous ammonium chloride solution.

The isolation of the purified midostaurin can be carried out by adding 2-MeTHF, dissolving by heating, crystallizing by cooling and subsequently filtering.

In order to better illustrate the present invention, without limiting it, the examples which are depicted herein after are now given.

EXAMPLES
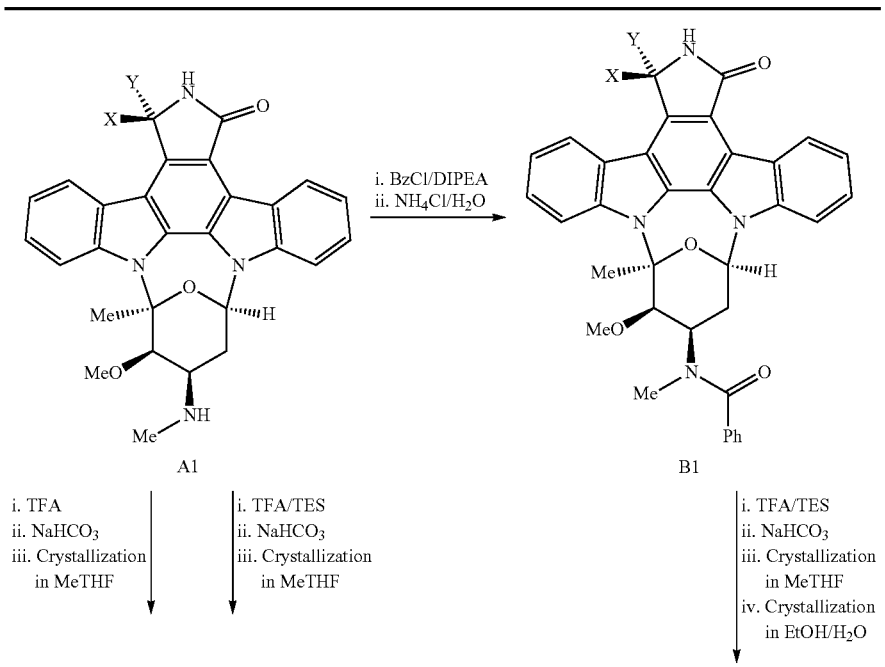
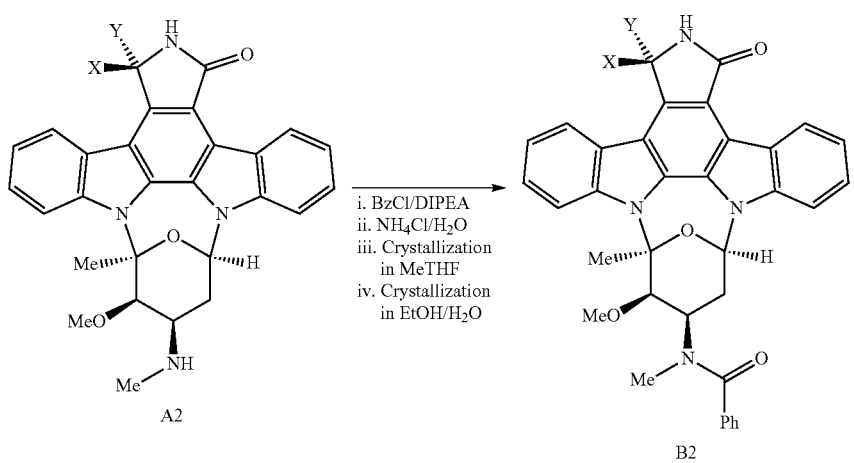
| Compound | (II) | (V) | (VI) | (I) | (III) | (IV) |
|---|---|---|---|---|---|---|
| A1 | >98% | >0.1% | >0.1% | — | — | — |
| A2 | >99% | <0.1% | <0.1% | — | — | — |
| B1 | <0.2% | — | — | >98% | >0.1% | >0.1% |
| B2 | <0.1% | — | — | >99% | <0.1% | <0.1% |

Example 1

Method for Obtaining Crude Midostaurin B1 from Crude Staurosporine A1

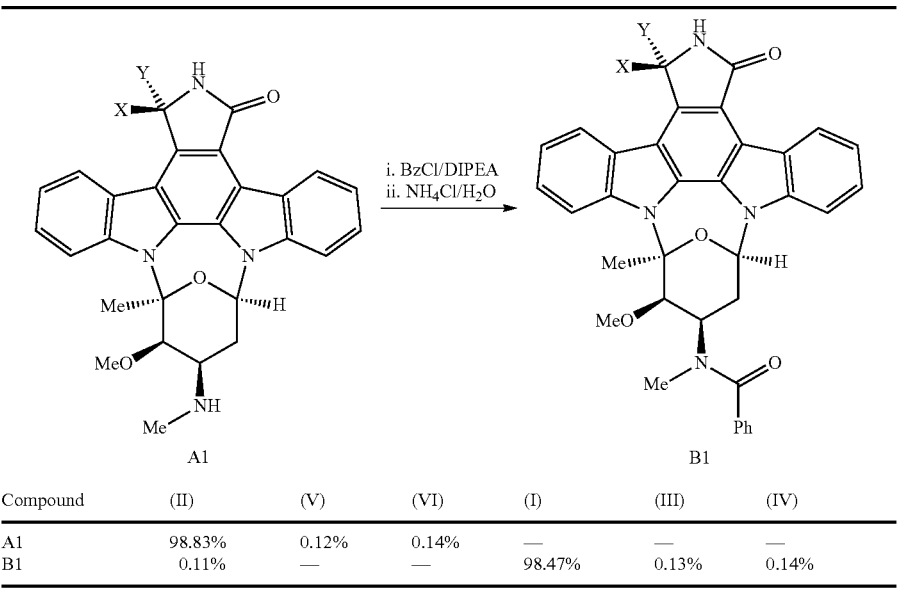

| Compound | (II) | (V) | (VI) | (I) | (III) | (IV) |
|---|---|---|---|---|---|---|
| A1 | 98.83% | 0.12% | 0.14% | — | — | — |
| B1 | 0.11% | — | — | 98.47% | 0.13% | 0.14% |

A reactor was loaded with crude staurosporine A1 (1 mol) and DMF (7 L). The solution was cooled to 0° C. and subsequently DIPEA (1.5 mol) was added. Benzoyl chloride (1.2 mol) was added while keeping the temperature within the range 0-5° C. After 30 minutes from the end of the addition, an aqueous 1% ammonium chloride solution (15 L) was added while keeping the temperature within the range 0-5° C. After 1 hour from the end of the addition, the suspension was filtered and the panel was washed with plenty of water. The solid was dried for 6 hours at 40° C., obtaining crude midostaurin 131 with 95% yield.

Example 2

Method for Obtaining Purified Midostaurin B2 from Crude Midostaurin B1-Reduction of 3-hydroxymidostaurin to Midostaurin with Triethylsilane

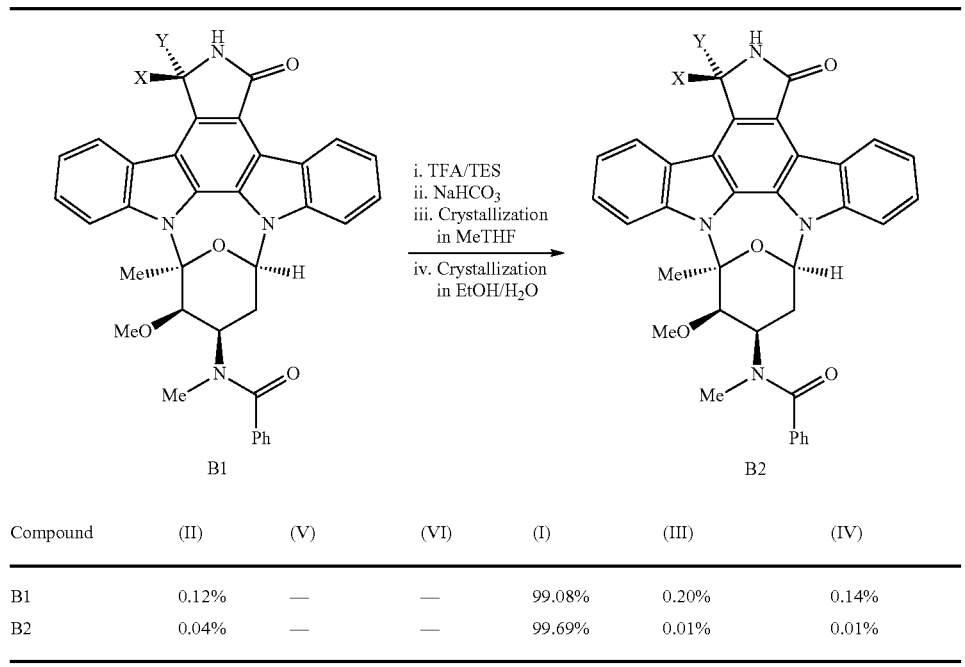

| Compound | (II) | (V) | (VI) | (I) | (III) | (IV) |
|---|---|---|---|---|---|---|
| B1 | 0.12% | — | — | 99.08% | 0.20% | 0.14% |
| B2 | 0.04% | — | — | 99.69% | 0.01% | 0.01% |

A reactor was loaded with crude midostaurin B1 (1 mol) and DCM (10 L). The solution was cooled to 0° C. and subsequently added with TES (1 mol) and TFA (0.50 L) in this order, while keeping the temperature within the range 0-5° C. At the end of the additions the solution was brought to 20° C. After 3 hours the solution was added with an aqueous 5% sodium bicarbonate solution (20 L). At the end of the development of gas the resulting two phases were separated and the aqueous phase was washed twice with DCM (10 L). The collected organic phases were concentrated at atmospheric pressure, added with 2-MeTHF (30 L) and two changes of solvent at atmospheric pressure were carried out. The solution was clarified by filtration at 75° C. and the panel was washed with 2-MeTHF. The filtrate was transferred into another reactor and cooled at 0° C. in 8 hours. After further 2 hours at 0° C. the suspension was filtered and the panel was washed twice with 2-MeTHF. The solid was dried for 12 hours at 80° C. and subsequently transferred into another reactor. Ethanol (7 L) was added and the mixture was heated at 75° C. up to complete dissolution. Water (30 L) was added with a concurrent cooling to 20° C. The resulting suspension was filtered and the panel was washed with plenty of water. The solid was dried for 12 hours at 80° C., obtaining purified midostaurin B2 with 85% yield.

Example 3

Method for Obtaining Purified Staurosporine A2 from Crude Staurosporine A1-Reduction of 3-hydroxystaurosporine to Staurosporine with Triethylsilane

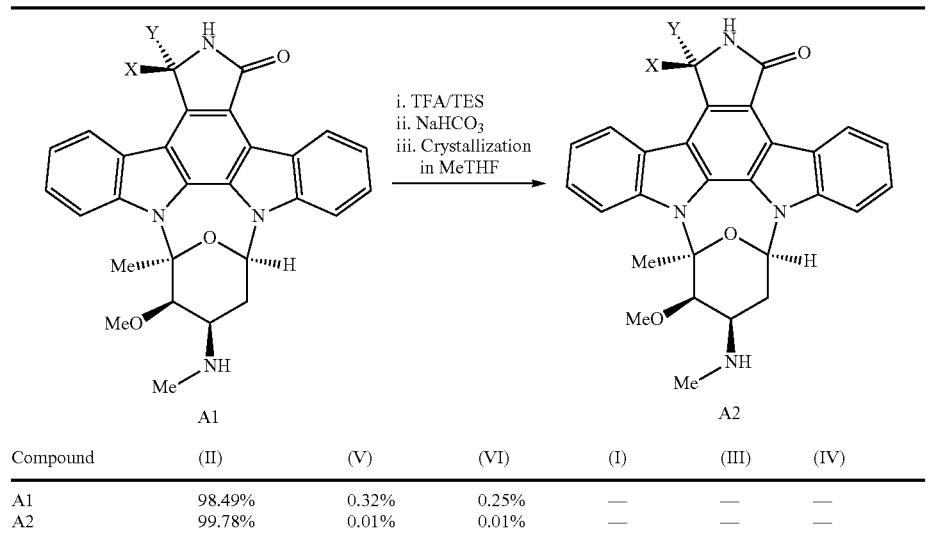

| Compound | (II) | (V) | (VI) | (I) | (III) | (IV) |
|---|---|---|---|---|---|---|
| A1 | 98.49% | 0.32% | 0.25% | — | — | — |
| A2 | 99.78% | 0.01% | 0.01% | — | — | — |

A reactor was loaded with crude staurosporine A1 (1 mol) and DCM (10 L). The solution was cooled to 0° C. and subsequently added with TES (1 mol) and TFA (0.50 L) in this order, while keeping the temperature within the range 0-5° C. After 1 hour from the end of the additions, the solution was added with MeOH (10 L) and, subsequently, with an aqueous 5% sodium bicarbonate solution (20 L). At the end of the development of gas the resulting two phases were separated and the aqueous phase was washed twice with DCM (10 L). The collected organic phases were concentrated at atmospheric pressure, added with 2-MeTHF (50 L) and two changes of solvent at atmospheric pressure were carried out. The warm solution was clarified by filtration at 75° C. and the panel was washed with 2-MeTHF. The filtrate was transferred into another reactor and cooled at 0° C. in 8 hours. After further 2 hours at 0° C. the suspension was filtered and the panel was washed twice with 2-MeTHF. The solid was dried for 12 hours at 80° C., obtaining purified staurosporine A2 with 80% yield.

Example 4

Method for Obtaining Purified Staurosporine A2 from Crude Staurosporine A1-Derivatization of 3-hydroxystaurosporine with Trifluoroacetic Acid and Purification by Crystallization

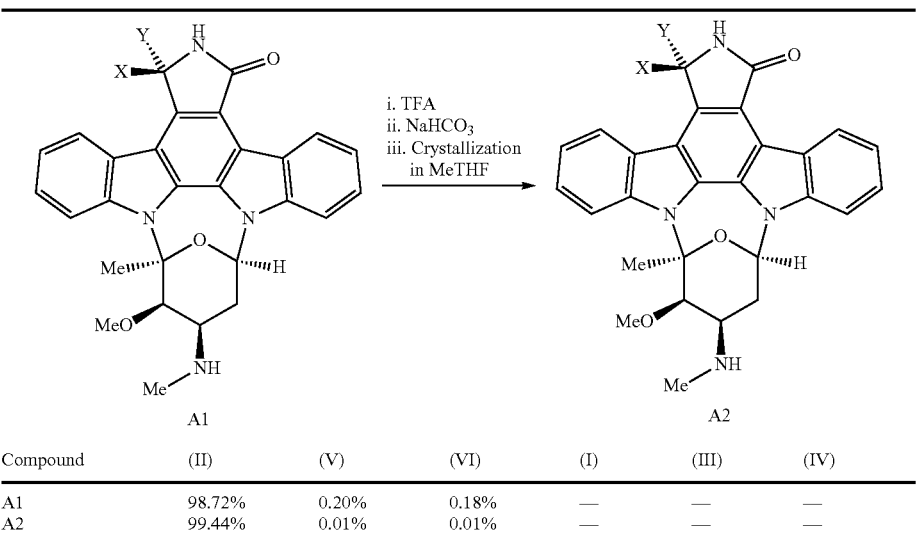

| Compound | (II) | (V) | (VI) | (I) | (III) | (IV) |
|---|---|---|---|---|---|---|
| A1 | 98.72% | 0.20% | 0.18% | — | — | — |
| A2 | 99.44% | 0.01% | 0.01% | — | — | — |

A reactor was loaded with crude staurosporine A1 (1 mol) and DCM (10 L). The mixture was cooled to 0° C. and added with TFA (0.50 L), while keeping the temperature within the range 0-5° C. After 1 hour from the end of the addition, the solution was added with MeOH (10 L) and, subsequently, with an aqueous 5% sodium bicarbonate solution (20 L). At the end of the development of gas the resulting two phases were separated and the aqueous phase was washed twice with DCM (10 L).

The collected organic phases were concentrated at atmospheric pressure, added with 2-MeTHF (50 L) and two changes of solvent at atmospheric pressure were carried out. The warm solution was clarified by filtration at 75° C. and the panel was washed with 2-MeTHF. The filtrate was transferred into another reactor and cooled at 0° C. in 8 hours. After further 2 hours at 0° C. the suspension was filtered and the panel was washed twice with 2-MeTHF. The solid was dried for 12 hours at 80° C., obtaining purified staurosporine A2 with 80% yield.

Example 5

Method for Obtaining Purified Midostaurin B2 from Purified Staurosporine A2

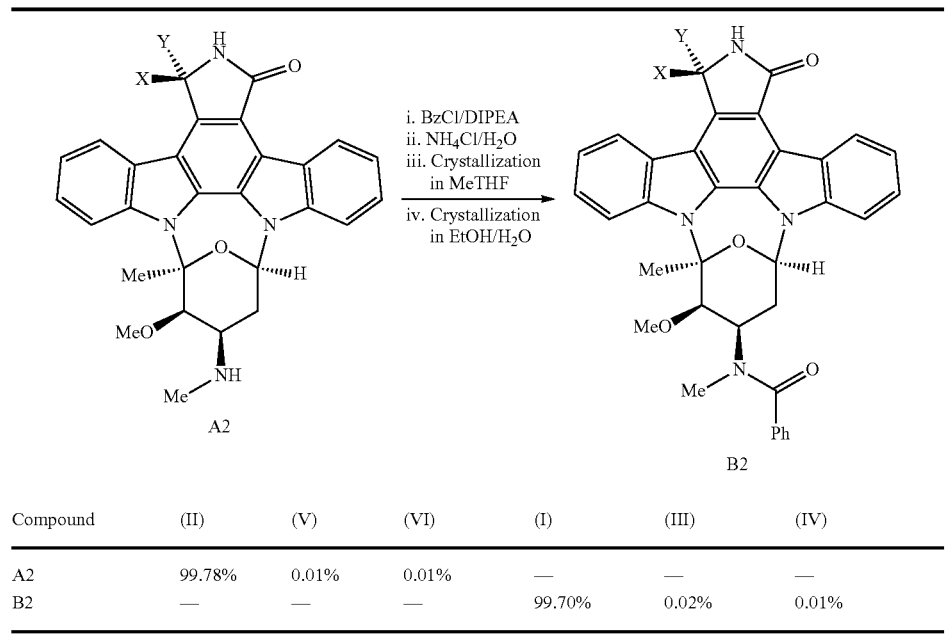

| Compound | (II) | (V) | (VI) | (I) | (III) | (IV) |
|---|---|---|---|---|---|---|
| A2 | 99.78% | 0.01% | 0.01% | — | — | — |
| B2 | — | — | — | 99.70% | 0.02% | 0.01% |

A reactor was loaded with purified staurosporine A2 (1 mol) and DMF (7 L). The solution was cooled to 0° C. and subsequently DIPEA (1.5 mol) was added. Benzoyl chloride (1.2 mol) was added while keeping the temperature within the range 0-5° C. After 30 minutes from the end of the addition, an aqueous 1% ammonium chloride solution (15 L) was added while keeping the temperature within the range 0-5° C. After 1 hour from the end of the addition, the suspension was filtered and the panel was washed with plenty of water. The solid was dried for 6 hours at 40° C. and subsequently transferred into another reactor. 2-MeTHF (30 L) was added and the suspension was heated under reflux up to complete dissolution. The solution was clarified by filtration at 75° C. and the panel was washed with 2-MeTHF. The filtrate was transferred into another reactor and cooled at 0° C. in 8 hours. After further 2 hours at 0° C. the suspension was filtered and the panel was washed twice with 2-MeTHF. The solid was dried for 12 hours at 80° C. and subsequently transferred into another reactor. Ethanol (7 L) was added and the mixture was heated at 75° C. up to complete dissolution. Water (30 L) was added with a concurrent cooling to 20° C. The resulting suspension was filtered and the panel was washed with plenty of water. The solid was dried for 12 hours at 80° C., obtaining purified midostaurin B2 with 85% yield.

The invention claimed is:

1. A process for the preparation of midostaurin with high purity, that is with a content of 3-hydroxymidostaurin impurities (III) and (IV) lower than 0.1%, comprising treating crude midostaurin with strong organic or inorganic acids in a water-immiscible solvent and, optionally, also with reducing silanes.

2. The process according to claim 1, further comprising treating the crude midostaurin with a reducing silane.

3. A process for the preparation of midostaurin with high purity, that is with a content of 3-hydroxymidostaurin impurities (III) and (IV) lower than 0.1%, comprising treating crude staurosporine with a strong organic or inorganic acid, optionally with the concomitant addition of a reducing silane.

4. The process according to claim 1, wherein the water-immiscible solvent is an aprotic polar water-immiscible solvent.

5. The process according to claim 4 wherein the water-immiscible solvent is dichloromethane, dichloroethane, methyl tetrahydrofuran or methylethylketone.

6. The process according to claim 1, wherein the strong acid is trifluoroacetic acid.

7. The process according to claim 1, wherein the reducing silane is triethylsilane.

8. The process according to claim 3, further comprising the benzoylation reaction of staurosporine to midostaurin wherein the benzoylation reaction is quenched with an aqueous solution having a slightly acid pH.

9. The process according to claim 8 wherein the aqueous solution having a slightly acid pH is an aqueous ammonium chloride solution.

10. The process of claim 1, wherein the purified midostaurin is obtained by crystallization from 2-MeTHF and is isolated by:
    dissolving the crystallized midostaurin in a water-miscible polar solvent,
    adding water
    isolating purified midostaurin as an amorphous solid obtained by filtering and drying, with a content of organic solvents <50 ppm.

11. The process for the preparation of purified midostaurin according to claim 10, wherein the polar solvent is ethanol.

12. The process according to claim 5, wherein the water-immiscible solvent is dichloromethane.

13. The process according to claim 3, wherein the water-immiscible solvent is an aprotic polar water-immiscible solvent.

14. The process according to claim 13 wherein the water-immiscible solvent is dichloromethane, dichloroethane, methyl tetrahydrofuran or methylethylketone.

15. The process according to claim 14, wherein the water-immiscible solvent is dichloromethane.

16. The process according to claim 3, wherein the strong acid is trifluoroacetic acid.

17. The process according to claim 3, wherein the reducing silane is triethylsilane.

* * * * *